(12) United States Patent
Dath et al.

(10) Patent No.: US 8,674,157 B2
(45) Date of Patent: *Mar. 18, 2014

(54) PRODUCTION OF OLEFINS

(75) Inventors: Jean-Pierre Dath, Beloeil (BE); Walter Vermeiren, Houthalen (BE)

(73) Assignee: Total Research & Technology Feluy, Seneffe (Feluy) (BG)

( * ) Notice: Subject to any disclaimer, the term of this patent is extended or adjusted under 35 U.S.C. 154(b) by 1133 days.

This patent is subject to a terminal disclaimer.

(21) Appl. No.: 10/569,240

(22) PCT Filed: Aug. 12, 2004

(86) PCT No.: PCT/EP2004/009142
§ 371 (c)(1),
(2), (4) Date: Sep. 29, 2006

(87) PCT Pub. No.: WO2005/016856
PCT Pub. Date: Feb. 24, 2005

(65) Prior Publication Data
US 2007/0027351 A1 Feb. 1, 2007

(30) Foreign Application Priority Data
Aug. 19, 2003 (EP) .................................. 03077639

(51) Int. Cl.
*C07C 1/24* (2006.01)
*C07C 4/06* (2006.01)

(52) U.S. Cl.
USPC ........... 585/634; 585/638; 585/639; 585/640; 585/648; 585/650; 585/651

(58) Field of Classification Search
USPC ......... 585/651–653, 639–640, 238, 239, 240, 585/638, 634, 648, 650; 208/109, 113, 114, 208/118, 120.01, 130
See application file for complete search history.

(56) References Cited

U.S. PATENT DOCUMENTS 4,542,252 A * 9/1985 Graziani et al. ............... 585/640
4,788,377 A * 11/1988 Chang et al. .................. 585/640
(Continued)

FOREIGN PATENT DOCUMENTS

DD 270 296 A 7/1989
WO 00/78894 A1 12/2000

OTHER PUBLICATIONS

Lucke, Berhard et al.: "CMHC: coupled methanol hydrocarbon cracking—Formation of lower olefins from methanol and hydrocarbons over modified zeolites", Microporous and Mesoporous Materials 29 (1999) 145-147, Elsevier Science Publishing, New York.*

(Continued)

*Primary Examiner* — In Suk Bullock
*Assistant Examiner* — Bradley Etherton (57) ABSTRACT

A process for converting a hydrocarbon feedstock to provide an effluent containing light olefins, the process comprising passing a hydrocarbon feedstock comprising a mixture of a first portion, containing one or more olfeins of $C_4$ or greater, and a second portion, containing at least one $C_1$ to $C_6$ aliphatic hetero compound selected from alcohols, ethers, carbonyl compounds and mixtures thereof, through a reactor containing a crystalline silicate catalyst to produce an effluent including propylene, the crystalline silicate being selected from at least one of an MFI-type crystalline silicate having a silicon/aluminum atomic ratio of at least 180 and an MEL-type crystalline silicate having a silicon/aluminum atomic ratio of from 150 to 800 which has been subjected to a steaming step.

20 Claims, 3 Drawing Sheets

(56) References Cited

U.S. PATENT DOCUMENTS

| | | | |
|---|---|---|---|
| 5,019,663 A * | 5/1991 | Chou et al. | 585/415 |
| 6,613,951 B1 * | 9/2003 | Brown et al. | 585/640 |
| 6,646,175 B1 * | 11/2003 | Dath et al. | 585/651 |
| 2003/0078463 A1 * | 4/2003 | Martens et al. | 585/638 |

OTHER PUBLICATIONS

Obenaus, et al., "Butenes" in Ullmann's Encyclopedia of Industrial Chemistry, Wiley-VCH, published on-line Jun. 15, 2000.*

International Search Report issued in International Application No. PCT/EP2004/009142 mailed on Nov. 10, 2004 (3 pages).

Japanese Office Action issued in Japanese Application No. 2006-523589 mailed on Dec. 14, 2010, and English translation thereof (6 pages).

Korean Office Action issued in Korean Application No. 10-2006-7003304 mailed on Mar. 22, 2011, and English translation thereof (13 pages).

Nowak, S. et al.: "An Improved Method for Producing Low Olefins and Gasoline by Coupled Methanol/Hydrocarbon Cracking (CMHC)" Proceeding of 9th International Congress on Catalysis, vol. 4, 1988, pp. 1735-42, XP008025672 Calgary.

Nowak, S. et al.: "Coupled Methanol/Hydrocarbon Cracking (CMHC)—New Route to Lower Olefins from Methanol" Chemical Industries, vol. 46, 1992, pp. 361-80, XP008025670, New York, NT, US, ISSN: 0737-8025.

Martin, a. et al.: "Coupled Conversion of Methanol and C4-Hydrocarbons (CMHC) on Iron-Containing ZSM-5 Type Zeolites" Applied Catalysis, vol. 57, No. 2, 1990, pp. 203-214, XP008025673, Amsterdam, NL, ISSN: 0166-9834.

* cited by examiner

PRODUCTION OF OLEFINS

The present invention relates to a process for converting a hydrocarbon feedstock to produce an effluent containing light olefins, in particular propylene.

There is an increasing demand for light olefins, for example ethylene and propylene, in the petrochemical industry, in particular for the production of polymers, in particular polyethylene and polypropylene. In particular, propylene has become an increasingly valuable product and accordingly there has been a need for the conversion of various hydrocarbon feedstocks to produce propylene.

Increasing amounts of stranded or associated natural gas are being found throughout the world. It becomes important to valorize these gas reserves, not only as fuel but if possible as a carbon source for chemicals and liquid transportable fuel. One way of doing this is the conversion of natural gas into synthesis gas and consequently synthesis of methanol that can serve as a primary source of other chemicals or liquid fuels.

It has been known for a number of years to convert low molecular weight monohydric alcohols such as methanol into light olefins, with the effluent containing ethylene and propylene. Methanol can readily be produced from methane present in natural gas, which is in abundant supply, and is in oversupply in some oil-producing regions of the world. There is therefore a need to produce light olefins such as ethylene and propylene from feedstocks derived from natural gas.

The conversion of a feed containing $C_1$ to $C_4$ monohydric alcohols to olefinic hydrocarbons including ethylene and propylene has been known at least since the 1970's. For example U.S. Pat. No. 4,148,835 in the name of Mobil Oil Corporation discloses a catalytic process for converting a feed containing a $C_1$-$C_4$ monohydric alcohol, in particular methanol, by contact of the alcohol, under conversion conditions, with a catalyst comprising a crystallised alumina silicate zeolite having a crystallite size at least about 1 micron, a silica to alumina ratio of at least about 12 and a constraint index within the approximate range of 1 to 12. In particular, the zeolite comprises ZSM 5. The effluent from the methanol conversion includes ethylene and propylene. The problem of the process disclosed in U.S. Pat. No. 4,148,835 is that the propylene yield is not very high and there is a need to increase the propylene yield of the conversion process.

EP-A-0123449 (and its equivalent U.S. Pat. No. 4,788,377), also in the name of Mobil Oil Corporation, disclose a process for converting alcohols/ethers, especially methanol, into olefins over zeolite catalysts. Olefin selectivity is enhanced by using zeolites of crystal size less than 1 micron and which have been steamed to alpha values of not more than 50, preferably 5 to 35. However, although the mixture of olefins produced contains mostly ethylene, propylene and the butylenes with a small pentenes component, there is no disclosure of a process which has a high propylene selectivity.

DE-A-2935863 (and its equivalent U.S. Pat. No. 4,849,753), also in the name of Mobil Oil Corporation, disclose a process for producing light olefins by catalytically converting methanol over crystalline aluminosilicate zeolites having high silica to alumina ratios at temperatures of from about 350 to 600° C. and at pressures ranging between about 1 and 100 atmospheres.

It is also known in the art to convert methanol to light olefins using a silica-alumina-phosphate catalyst, known as SAPO catalysts. It was considered that such catalysts had a higher selectivity to light olefins than the alumino-silicate zeolite catalysts employed in, for example, U.S. Pat. No. 4,148,835. For example, U.S. Pat. No. 4,861,938, U.S. Pat. No. 5,126,308 and EP-A-0558839, all in the name of UOP, each disclose a process for the conversion of methanol into light olefins, in particular ethylene and propylene, using a silica-alumina-phosphate catalyst, in particular SAPO 34. These processes suffer from the problem that, in particular, when used in a fixed reactor, the selectivity to propylene of the catalyst is poor, and additionally too much ethylene is produced, leading to a relatively low propylene/ethylene molar ratio. This lowers the propylene purity in a fractionated cut containing $C_2$ and $C_3$ hydrocarbons. Also, as a result of the production of propane, the propylene purity in a $C_3$ cut may be low. Furthermore, the propylene selectivity tends not to be stable over time. There is therefore a need to provide a conversion process which has a higher propylene selectivity than these known processes.

EP-A-0882692 discloses a process for the production of lower olefins with 2-3C atoms which comprises reacting a methanol and/or dimethylether vapour and a reaction mixture containing water vapour in a first reactor on a first form selective catalyst at 280-570° C. and 0.1-1 bar; withdrawing a product mixture containing 2-4C olefin and 5C+ hydrocarbon from the first reactor; and cooling. The cooled first product mixture is fed through a separator and a second product mixture containing ethylene and propylene is withdrawn. A 5C+ stream is obtained, which is vaporised and mixed with water vapour. A ratio of $H_2O$:hydrocarbons of 0.5-3:1 is used. The mixture containing water vapour is fed at 380-700° C. to a second reactor containing a second form selective catalyst. A third product mixture is withdrawn from the second reactor which contains 50% olefinic components. This product mixture is cooled and fed to a separator. The catalyst in the first reactor may be a zeolite as disclosed in EP-B-0448000, a SAPO catalyst as disclosed in U.S. Pat. No. 4,524,235 and EP-A-0142156, or a silicalite catalyst as disclosed in U.S. Pat. No. 4,061,724. The catalyst in the second reactor may be a zeolite of the Pentasil-type having a silicon/aluminium atomic ratio of from 10:1 to 200:1, variants of such catalysts being disclosed in EP-B-0369364, a SAPO catalyst or a silicalite catalyst.

It is also known to crack catalytically an olefin-containing feedstock using a crystalline silicate catalyst, for example from WO-A-99/29802. It would be desirable to improve the flexibility of this process with regard to the feedstocks to be used and to improve the propylene purity of the effluent. Also, it would be desirable to be able to improve the heat balance of the reactor used for the catalytic cracking process.

It is ether known to use a crystalline silicate cracking catalyst to produce light olefins such as ethylene. For example, WO-A-98/56877 discloses a process for improving the conversion of a light hydrocarbon feedstock to light olefins comprising the steps of first contacting the hydrocarbon feedstock with a light olefin producing cracking catalyst, such as a ZSM-5 zeolite, and subsequently thermally cracking the unseparated stream to produce additional ethylene.

In a first paper entitled "CMHC: coupled methanol hydrocarbon cracking. Formation of lower olefins from methanol and hydrocarbons over modified zeolites" by Bernhard Lucke et al, Microporous and Mesoporous Materials, 29 (1999) 145-157 (Elsevier Science Publishing, New York, USA, 06-99, 29 (1-2) (XP4167556) it is disclosed that coupled methanol hydrocarbon cracking was carried out using, inter alia, $C_4$ olefins (in particular iso-butene or a mixture of 45% iso-butene, 27% n-butene-(1), 15% n-butene-(2) and 13% n-+i-butane) co-fed with methanol (Table 3). The catalyst was a zeolite with an MFI structure (H-ZSM-5) with a Si/Al ratio (after synthesis) of about 16-30. The temperature was 873 K or 953 K. The effluent contained ethylene and propylene, as well as BTX aromatics, methane and others. However, the time-on-stream was only a few hours. The authors noted that the parent H-ZSM-5 zeolite samples were subjected to fast deactivation due to rapid coking and dealumination and proposed a number of routes to modify the zeolite to increase the deactivation resistance. One of these routes was to steam the catalyst at 775K (denoted by "D" for "dealumination").

A second paper, by three of the same authors as the first paper, entitled "Coupled methanol/hydrocarbon cracking (CMHC)—A new route to lower olefins from methanol" by S. Nowak et al, Chemical Industries (1992), 46, 361-80, XP8025670) similarly discloses the use of an industrial H-ZSM-5 zeolite with a Si/Al ratio of 16, and some catalyst samples had been pretreated by dealumination by steam treatment with subsequent acid leaching to rearrange the extra-framework Al formed.

In a further paper by substantially the same authors entitled "An improved method for producing lower olefins and gasoline by coupled methanol/hydrocarbon cracking (CHMC)" by S. Nowak et al, Proceedings of $9^{th}$ International Congress on Catalysis, (1988), 4, 1735-42 (XP8025672), the catalyst was an H-ZSM-5 zeolite with a $SiO_2/Al_2O_3$ ratio (after synthesis) of 31-55. For a methanol/1-butene or $C_4$ fraction feed (FIG. 6) the results are the same as for Table 3 of document (XP4167556) discussed above.

In a yet further paper entitled "Coupled conversion of methanol and C4 hydrocarbons (CHMC) on iron-containing ZSM-5 type zeolites" by A. Martin et al Applied Catalysis, 57, (1990) 203-214 (Elsevier Science Publishers B.V., Amsterdam, Netherlands (XP8025673), substantially the same authors iron-containing and iron-aluminium-containing ZSM-% catalysts were used, and one comparative catalyst had a Si/Al ratio of 22.

DD-A-270296 (having as inventors substantially the same persons as the authors of the above four papers) discloses a process for producing lower olefins using a Fe—Al—Si zeolite catalyst.

It is an object of the present invention to provide a process for converting olefinic feedstocks having a high yield on an olefin basis towards propylene, irrespective of the origin and composition of the olefinic feedstock.

It is a further object of the present invention to provide a process for converting oxygen-containing hydrocarbon feedstocks which has a high yield of lighter olefins, and in particular propylene.

It is another object of the invention to provide a process for producing propylene having a high propylene yield and purity.

It is a further object of the present invention to provide such a process which can produce a propylene-containing effluent which is within, at least, a chemical grade quality.

It is yet a further object of the present invention to provide a process for producing propylene having a stable propylene conversion and a stable product distribution over time.

The present invention provides a process for converting a hydrocarbon feedstock to provide an effluent containing light olefins, the process comprising passing a hydrocarbon feedstock comprising a mixture of a first portion, containing one or more olefins of $C_4$ or greater, and a second portion, containing at least one $C_1$ to $C_6$ aliphatic hetero compound selected from alcohols, ethers, carbonyl compounds and mixtures thereof, through a reactor containing a crystalline silicate catalyst to produce an effluent including propylene, the crystalline silicate being selected from at least one of an MFI-type crystalline silicate having a silicon/aluminium atomic ratio of at least 180 and an MEL-type crystalline silicate having a silicon/aluminium atomic ratio of from 150 to 800 which has been subjected to a steaming step.

Preferably, the weight ratio of the at least one $C_1$ to $C_6$ aliphatic hetero compound in the second portion to the total hydrocarbons in the first and second portions of the feedstock is from 1 to 99%, more preferably from 15 to 85%, yet more preferably from 25 to 50%.

Preferably, the weight ratio of the at least one $C_1$ to $C_6$ aliphatic hetero compound in the second portion to the total unsaturated hydrocarbons in the first portion of the feedstock is from 0.05:1 to 20:1, more preferably from 0.25:1 to 4:1, yet more preferably from 0.5:1 to 2:1, most preferably from 0.75:1 to 1:1.

Preferably, the second portion of the hydrocarbon feedstock contains at least one of methanol, ethanol, dimethyl ether, diethyl ether and mixtures thereof.

More preferably, the second portion of the hydrocarbon feedstock comprises methanol.

Preferably, the reactor is additionally fed with steam.

Preferably, the hydrocarbon feedstock contains up to 80 wt % steam.

Preferably, the hydrocarbon feedstock is passed over the crystalline silicate at a reactor inlet temperature of from 350 to 650° C.

More preferably, the hydrocarbon feedstock is passed over the crystalline silicate at a reactor inlet temperature of 400 to 600° C., yet more preferably from 460 to 580° C., and most preferably from 540 to 560° C.

Preferably, the hydrocarbon feedstock is passed over the crystalline silicate at a LHSV of from 0.5 to 30 $h^{-1}$, more preferably from 1 to 20 $h^{-1}$.

Preferably, the partial pressure of the at least one or more olefins in the feedstock when passed over the crystalline silicate is from 10 to 200 kPa.

Preferably, the partial pressure of the at least one $C_1$ to $C_6$ aliphatic hetero compound in the feedstock when passed over the crystalline silicate is from 10 to 400 kPa, more preferably from 20 to 380 kPa, most preferably about 100 kPa.

Preferably, the total absolute pressure is from 0.5 to 50 bars, more preferably from 5 to 45 bars.

Preferably, the crystalline silicate catalyst comprises silicalite having a silicon/aluminium atomic ratio of from 250 to 500.

Preferably, the first portion of the hydrocarbon feedstock includes at least one of a hydrotreated raw $C_4$ feedstock, LCCS, a raffinate 2 feedstock, a raffinate 1 feedstock, a raffinate 2 feedstock from a methyl tert-butyl ether (MTBE) or an ethyl tert-butyl ether (ETBE) unit, a raffinate from an olefins metathesis unit, in particular for the production of propylene from ethylene and butene, or a hydrotreated olefin-containing stream from an FCC unit, a visbreaker or a delayed coker.

Additionally or alternatively, the first portion of the hydrocarbon feedstock includes a product, which contains $C_4+$ olefins, of a methanol-to-olefins (MTO) process Optionally, a fraction, which contains $C_4+$ olefins, of the effluent is recycled back through the reactor thereby to constitute at least a part of the first portion of the hydrocarbon feedstock.

The present invention also provides the use, in a process for catalytic cracking of olefins in a hydrocarbon feed over a crystalline silicate catalyst of the MFI-type having a silicon/aluminium atomic ratio of from 250 to 500 in a reactor to produce an effluent including propylene, of a co-injection of a second feed containing at least one $C_1$ to $C_6$ aliphatic hetero compound selected from alcohols, ethers, carbonyl compounds and mixtures thereof, for making the heat balance in the reactor more uniform.

The present invention further provides the use, in a process for catalytic cracking of olefins in a hydrocarbon feed over a crystalline silicate catalyst of the MFI-type having a silicon/aluminium atomic ratio of from 250 to 500 in a reactor to produce an effluent including propylene, of a co-injection of a second feed containing at least one $C_1$ to $C_6$ aliphatic hetero compound selected from alcohols, ethers, carbonyl compounds and mixtures thereof, for increasing the propylene/ethylene ratio in the effluent.

The present invention still further provides the use, in a process for catalytic cracking of olefins in a hydrocarbon feed over a crystalline silicate catalyst of the MFI-type having a silicon/aluminium atomic ratio of from 250 to 500 in a reactor to produce an effluent including propylene, of a co-injection of a second feed containing at least one $C_1$ to $C_6$ aliphatic hetero compound selected from alcohols, ethers, carbonyl compounds and mixtures thereof, for increasing the propylene/propane ratio in a $C_3$ cut from the effluent.

In any such use, preferably the second feed includes methanol, the hydrocarbon feed contains one or more olefins of $C_4$ or greater, the weight ratio of the methanol in the second feed to the total unsaturated hydrocarbons in the hydrocarbon feed is from 0.5:1 to 2:1, and the reactor inlet temperature is from 540 to 560° C.

The present invention can thus provide a process wherein hydrocarbon streams (products) from refinery and petrochemical plants are selectively converted not only into light olefins, but particularly into propylene.

The hydrocarbon feedstock may be fed either undiluted or diluted with steam and/or an inert gas such as nitrogen. In the latter case, the absolute pressure of the feedstock constitutes the partial pressure of the hydrocarbon feedstock in the steam and/or the inert gas.

The various aspects of embodiments of the present invention will now be described in greater detail, by way of example only, with reference to the accompanying drawings, in which.

The process of the present invention comprises passing a hydrocarbon feedstock, comprising a mixture of a first portion, containing one or more olefins of $C_4$ or greater, and a second portion, containing at least one $C_1$ to $C_6$ aliphatic hetero compounds selected from alcohols, ethers, carbonyl compounds and mixtures thereof, through a reactor containing such a crystalline silicate catalyst, in order to produce an effluent containing light olefins, particularly propylene.

The catalytic cracking of olefins is performed in the sense that olefins in the olefin-containing first portion of the combined hydrocarbon stream are cracked into lighter olefins and selectively into propylene. The olefin-containing portion of feedstock may comprise any kind of olefin-containing hydrocarbon stream. The olefin-containing portion of the feedstock may typically comprise from 10 to 100 wt % olefins and furthermore may be fed undiluted or diluted by a diluent, the diluent optionally including a non-olefinic hydrocarbon. In particular, the olefin-containing portion may be a hydrocarbon mixture containing normal and branched olefins in the carbon range $C_4$ to $C_{10}$, more preferably in the carbon range $C_4$ to $C_6$, optionally in a mixture with normal and branched paraffins and/or aromatics in the carbon range $C_4$ to $C_{10}$. Typically, the olefin-containing stream has a boiling point of from around −15° C. to around 180° C.

In particularly preferred embodiments of the present invention, the olefin-containing portion of the hydrocarbon feedstocks may comprise $C_4$ mixtures from refineries and steam cracking units. Such steam cracking units crack a wide variety of feedstocks, including ethane, propane, butane, naphtha, gas oil, fuel oil, etc. Most particularly, the olefin-containing portion of the hydrocarbon feedstock may comprises a $C_4$ cut from a fluidized-bed catalytic cracking (FCC) unit in a crude oil refinery which is employed for converting heavy oil into gasoline and lighter products. Typically, such a $C_4$ cut from an FCC unit comprises around 50 wt % olefin. Alternatively, the olefin-containing portion of the hydrocarbon feedstock may comprise a $C_4$ cut from a unit within a crude oil refinery for producing methyl tert-butyl ether (MTBE) which is prepared from methanol and isobutene. Again, such a $C_4$ cut from the MTBE unit typically comprises around 50 wt % olefin. These $C_4$ cuts are fractionated at the outlet of the respective FCC or MTBE unit. The olefin-containing portion of the hydrocarbon feedstock may yet further comprise a $C_4$ cut from a naphtha steam-cracking unit of a petrochemical plant in which naphtha, comprising $C_5$ to $C_9$ species having a boiling point range of from about 15 to 180° C., is steam cracked to produce, inter alia, a $C_4$ cut. Such a $C_4$ cut typically comprises, by weight, 40 to 50% 1,3-butadiene, around 25% isobutylene, around 15% butene (in the form of but-1-ene and/or but-2-ene) and around 10% n-butane and/or isobutane. The olefin-containing portion of the hydrocarbon feedstock may also comprise a $C_4$ cut from a steam cracking unit after butadiene extraction (raffinate 1), or after butadiene hydrogenation, thereby comprising a hydrotreated $C_4$ stream (known in the art as a "hydrotreated raw $C_4$" stream), or a raw $C_4$ feedstock, or a raffinate 2 feedstock from an MTBE or an ethyl tert-butyl ether (ETBE) unit, or a raffinate from an olefins metathesis unit.

The olefin-containing portion of the feedstock may yet further alternatively comprise a hydrogenated butadiene-rich $C_4$ cut, typically containing greater than 50 wt % $C_4$ as an olefin. Alternatively, the olefin-containing portion of the hydrocarbon feedstock could comprise a pure olefin feedstock which has been produced in a petrochemical plant.

The olefin-containing portion of the feedstock may yet further alternatively comprise light cracked naphtha (LCN) (otherwise known as light catalytic cracked spirit (LCCS)) or a $C_5$ cut from a steam cracker or light cracked naphtha, the light cracked naphtha being fractionated from the effluent of the FCC unit, discussed hereinabove, in a crude oil refinery. Both such feedstocks contain olefins. The olefin-containing portion of the feedstock may yet further alternatively comprise a medium cracked naphtha from such an FCC unit or visbroken naphtha obtained from a visbreaking unit for treating the residue of a vacuum distillation unit in a crude oil refinery or a coker naphtha. The olefin-containing portion of the feedstock may alternatively comprise a raffinate 2 feedstock, containing olefins but having a high isoparaffin content.

The olefin-containing portion of the feedstock may alternatively comprise or include a product, which contains $C_4+$ olefins, of a methanol-to-olefins (MTO) process, for example as described in U.S. Pat. No. 4,148,835, EP-A-0123449, and DE-A-2935863, and its equivalent U.S. Pat. No. 4,849,753 discussed hereinabove. A fraction, which contains $C_4+$ olefins, of the effluent of the process of the present invention may be recycled back through the reactor thereby to constitute at least a part of the olefin feed for the process of the invention.

The olefin-containing portion of the feedstock may comprise a mixture of one or more of the above-described feedstocks.

The use of a $C_5$ cut as or in the olefin-containing portion of the hydrocarbon feedstock has particular advantages because of the need to remove $C_5$ species in any event from gasolines produced by the oil refinery. This is because the presence of $C_5$ in gasoline increases the ozone potential and thus the photochemical activity of the resulting gasoline. In the case of the use of light cracked naphtha as the olefin-containing portion of the feedstock, the olefin content of the remaining gasoline fraction is reduced, thereby reducing the vapour pressure and also the photochemical activity of the gasoline.

The catalytic conversion of the second portion of the hydrocarbon steam containing at least one $C_1$ to $C_6$ aliphatic hetero compound selected from alcohols, ethers, carbonyl compounds and mixture thereof, is performed to produce in the effluent light olefins, in particular ethylene and propylene, and selectively propylene.

The $C_1$ to $C_6$ aliphatic alcohols may be monohydric and straight or branched and may be selected from methanol, ethanol, propanol and butanol. The ethers may be $C_2$ to $C_4$ ethers selected from dimethyl ether, diethyl ether or methyl ethyl ether. The carbonyl compounds may be $C_2$ to $C_4$ carbonyl compounds selected from formaldehyde, dimethyl ketone, or acetic acid. The second portion of the feedstock is most preferably selected from methanol, ethanol, dimethyl ether, diethyl ether and mixtures thereof, with methanol being particularly preferred.

In accordance with the process of the invention, the combined hydrocarbon feedstocks containing the first and second portions, are selectively converted in the presence of an MFI-type or MEL-type catalyst so as to produce propylene in the resultant effluent. The catalyst and process conditions are selected whereby the process has a particular yield towards propylene in the effluent.

In accordance with a preferred aspect of the present invention, the catalyst comprises a crystalline silicate of the MFI family which may be a zeolite, a silicalite or any other silicate in that family or the MEL family which may be a zeolite or any other silicate in that family. The three-letter designations "MFI" and "MEL" each represent a particular crystalline silicate structure type as established by the Structure Commission of the International Zeolite Association. Examples of MFI silicates are ZSM-5 and silicalite. An example of an MEL zeolite is ZSM-11 which is known in the art. Other examples are Boralite D, and silicalite-2 as described by the International Zeolite Association (Atlas of zeolite structure types, 1987, Butterworths).

The preferred crystalline silicates have pores or channels defined by ten oxygen rings and a high silicon/aluminium atomic ratio.

Crystalline silicates are microporous crystalline inorganic polymers based on a framework of $XO_4$ tetrahedra linked to each other by sharing of oxygen ions, where X may be trivalent (e.g. Al, B, ...) or tetravalent (e.g. Ge, Si, ...). The crystal structure of a crystalline silicate is defined by the specific order in which a network of tetrahedral units are linked together. The size of the crystalline silicate pore openings is determined by the number of tetrahedral units, or, alternatively, oxygen atoms, required to form the pores and the nature of the cations that are present in the pores. They possess a unique combination of the following properties: high internal surface area; uniform pores with one or more discrete sizes; ion exchangeability; good thermal stability; and ability to adsorb organic compounds. Since the pores of these crystalline silicates are similar in size to many organic molecules of practical interest, they control the ingress and egress of reactants and products, resulting in particular selectivity in catalytic reactions. Crystalline silicates with the MFI structure possess a bi-directional intersecting pore system with the following pore diameters: a straight channel along [010]: 0.53-0.56 nm and a sinusoidal channel along [100]:0.51-0.55 nm. Crystalline silicates with the MEL structure possess a bi-directional intersecting straight pore system with straight channels along [100] having pore diameters of 0.53-0.54 nm.

The crystalline silicate catalyst has structural and chemical properties and is employed under particular reaction conditions whereby the catalytic conversion to form light olefins, in particular propylene, readily proceeds.

The catalyst has a high silicon/aluminium atomic ratio, whereby the catalyst has relatively low acidity. In this specification, the term "silicon/aluminium atomic ratio" is intended to mean the Si/Al atomic ratio of the overall material, which may be determined by chemical analysis. In particular, for crystalline silicate materials, the stated Si/Al ratios apply not just to the Si/Al framework of the crystalline silicate but rather to the whole material.

Different reaction pathways can occur on the catalyst. Hydrogen transfer reactions are directly related to the strength and density of the acid sites on the catalyst, and such reactions are preferably suppressed by the use of high Si/Al ratios so as to avoid the formation of coke during the conversion process, thereby increasing the stability of the catalyst. Moreover, the use of high Si/Al atomic ratios has been found to increase the propylene selectivity of the catalyst, i.e. to reduce the amount of propane produced and/or to increase the propylene/ethylene ratio. This increases the purity of the resultant propylene.

In accordance with one aspect, a first type of MFI catalyst has a high silicon/aluminum atomic ratio, e.g. at least about 180, preferably greater than about 200, more preferably greater than about 250, whereby the catalyst has relatively low acidity. Hydrogen transfer reactions are directly related to the strength and density of the acid sites on the catalyst, and such reactions are preferably suppressed so as to avoid the progressive formation of coke which in turn would otherwise decrease the stability of the catalyst over time. Such hydrogen transfer reactions tend to produce saturates such as paraffins, intermediate unstable dienes and cyclo-olefins, and aromatics, none of which favours conversion into light olefins. Cyclo-olefins are precursors of aromatics and coke-like molecules, especially in the presence of solid acids, i.e. an acidic solid catalyst. The acidity of the catalyst can be determined by the amount of residual ammonia on the catalyst following contact of the catalyst with ammonia which adsorbs to the acid sites on the catalyst with subsequent ammonium desorption at elevated temperature measured by differential thermogravimetric analysis. Preferably, the silicon/aluminum ratio ranges from 180 to 1000, most preferably from 250 to 500.

With such high silicon/aluminum ratio in the crystalline silicate catalyst, a stable conversion of the hydrocarbon feedstock can be achieved, with a high propylene yield. Such high silicon/aluminum ratios in the catalyst reduce the acidity of the catalyst, thereby also increasing the stability of the catalyst.

The MFI catalyst having a high silicon/aluminum atomic ratio for use in the catalytic conversion process of the present invention may be manufactured by removing aluminum from a commercially available crystalline silicate. A typical commercially available silicalite has a silicon/aluminum atomic ratio of around 120. The commercially available MFI crystalline silicate may be modified by a steaming process which reduces the tetrahedral aluminum in the crystalline silicate framework and converts the aluminum atoms into octahedral aluminum in the form of amorphous alumina. Although in the steaming step aluminum atoms are chemically removed from the crystalline silicate framework structure to form alumina particles, those particles cause partial obstruction of the pores or channels in the framework. This inhibits the conversion processes of the present invention. Accordingly, following the steaming step, the crystalline silicate is subjected to an extraction step wherein amorphous alumina is removed from the pores and the micropore volume is, at least partially, recovered. The physical removal, by a leaching step, of the amorphous alumina from the pores by the formation of a water-soluble aluminum complex yields the overall effect of de-alumination of the MFI crystalline silicate. In this way by removing aluminum from the MFI crystalline silicate framework and then removing alumina formed therefrom from the pores, the process aims at achieving a substantially homogeneous de-alumination throughout the whole pore surfaces of the catalyst. This reduces the acidity of the catalyst, and thereby reduces the occurrence of hydrogen transfer reactions in the conversion process. The reduction of acidity ideally occurs substantially homogeneously throughout the pores defined in the crystalline silicate framework. This is because in the hydrocarbon conversion process hydrocarbon species can enter deeply into the pores. Accordingly, the reduction of acidity and thus the reduction in hydrogen transfer reactions which would reduce the stability of the MFI catalyst are pursued throughout the whole pore structure in the framework. The framework silicon/aluminum ratio may be increased by this process to a value of at least about 180, preferably from about 180 to 1000, more preferably at least 200, yet more preferably at least 250, and most preferably from 250 to 500.

In the two papers entitled "CMHC: coupled methanol hydrocarbon cracking. Formation of lower olefins from methanol and hydrocarbons over modified zeolites" by Bernhard Lucke et al, Microporous and Mesoporous Materials, 29 (1999) 145-157 (Elsevier Science Publishing, New York, USA, 06-99, 29 (1-2) (XP4167556) and "Coupled methanol/hydrocarbon cracking (CMHC)—A new route to lower olefins from methanol" by S. Nowak et al, Chemical Industries (1992), 46, 361-80, P8025670), although it is disclosed that coupled methanol hydrocarbon cracking was carried out using a zeolite catalyst that had been subjected to "dealumination by steam treatment (with subsequent acid leaching) to rearrange the extra-framework Al formed", there is no disclosure or suggestion in those documents of increasing the Si/Al ratio in the catalyst, as defined in the present specification, to be within the range of at least 180. In the present specification, as stated above, the term "silicon/aluminium atomic ratio" is intended to mean the Si/Al atomic ratio of the overall material, which may be determined by chemical analysis. In particular, for crystalline silicate materials, the stated Si/Al ratios apply not just to the Si/Al framework of the crystalline silicate but rather to the whole material. In the two prior papers, dealumination in the sense of removing framework aluminium is disclosed, but not increasing the Si/Al ratio of the whole material to within the range of at least 180.

Instead of an MFI-type catalyst, the process of the invention may use an MEL-type crystalline silicate having a silicon/aluminium atomic ratio of from 150 to 800 which has been subjected to a steaming step. In accordance with this further aspect, an MEL catalyst for use in the catalytic hydrocarbon conversion process may be manufactured by steaming an as-synthesised or commercially available crystalline silicate. The MEL crystalline silicate catalyst for use in the invention most typically comprises a ZSM-11 catalyst which may be synthesised either using diaminooctane as the templating agent and sodium silicate as the silicon source or tetrabutyl phosphonium bromide as the templating agent and a silica sol as the silicon source.

Thus the ZSM-11 catalyst may be prepared by mixing sodium silicate with 1,8 diaminooctane together with aluminium sulphate to form a hydrogel which is then allowed to crystallise to form the crystalline silicate. The organic template material is then removed by calcining. Alternatively, the ZSM-11 catalyst is produced by reacting tetrabutyl phosphonium bromide and sodium hydroxide together with the silica sol prepared from colloidal silica. Again, a crystallisation is performed to produce the crystalline silicate and then the product is calcined.

In order to reduce the sodium content of the MEL crystalline silicate, the crystalline silicate is subjected to an ion exchange with a salt. Thereafter the material is dried. Typically, the crystalline silicate is subjected to ion exchange with ammonium ions, for example by immersing the crystalline silicate in an aqueous solution of $NH_4Cl$ or $NH_4NO_3$. Such an ion exchange step is desirable if the amount of sodium ions present in the crystalline silicate is so high that a crystalline sodium silicate phase is formed following calcination of the crystalline silicate which would be difficult to remove.

The initial MEL crystalline silicate may be modified by a steaming process which, without being bound by theory, is believed to reduce the tetrahedral aluminium in the crystalline silicate framework and to convert the aluminium atoms into octahedral aluminium in the form of amorphous alumina. Although in the steaming step aluminium atoms are chemically removed from the MEL crystalline silicate framework structure to form alumina particles, those particles appear not to migrate and so do not cause partial obstruction of the pores or channels in the framework which would otherwise inhibit the conversion processes of the present invention. The steaming step has been found to improve significantly the propylene yield, propylene selectivity and catalyst stability in the catalytic conversion process.

The steam treatment on the MEL catalyst is conducted at elevated temperature, preferably in the range of from 425 to 870° C., more preferably in the range of from 540 to 815° C. and at atmospheric pressure and at a water partial pressure of from 13 to 200 kPa. Preferably, the steam treatment is conducted in an atmosphere comprising from 5 to 100% steam. The steam treatment is preferably carried out for a period of from 1 to 200 hours, more preferably from 20 hours to 100 hours. As stated above, the steam treatment tends to reduce the amount of tetrahedral aluminium in the crystalline silicate framework, by forming alumina.

Following the steaming step, the MEL catalyst is thereafter calcined, for example at a temperature of from 400 to 800° C. at atmospheric pressure for a period of from 1 to 10 hours.

Following the steaming step, the MEL catalyst may be contacted by a complexing agent for aluminium which may comprise an acid in an aqueous solution thereof or a salt of such an acid or a mixture of two or more such acids or salts. The complexing agent may in particular comprise an amine, such as ethyl diamine tetraacetic acid (EDTA) or a salt thereof, in particular the sodium salt thereof. Following the contacting of the MEL crystalline silicate by the complexing agent, the crystalline silicate may be subjected to a second ion exchange step for reducing the sodium content of the crystalline silicate still further, for example by contacting the catalyst with an ammonium nitrate solution.

The MEL or MFI crystalline silicate catalyst may be mixed with a binder, preferably an inorganic binder, and shaped to a desired shape, e.g. extruded pellets. The binder is selected so as to be resistant to the temperature and other conditions employed in the catalyst manufacturing process and in the subsequent catalytic conversion process. The binder is an inorganic material selected from clays, silica, metal oxides such as $ZrO_2$ and/or metals, or gels including mixtures of silica and metal oxides. The binder is preferably alumina-free. However, aluminium in certain chemical compounds as in $AlPO_4$'s may be used as the latter are quite inert and not acidic in nature. If the binder which is used in conjunction with the crystalline silicate is itself catalytically active, this may alter the conversion and/or the selectivity of the catalyst. Inactive materials for the binder may suitably serve as diluents to control the amount of conversion so that products can be obtained economically and orderly without employing other means for controlling the reaction rate. It is desirable to provide a catalyst having a good crush strength. This is because in commercial use, it is desirable to prevent the catalyst from breaking down into powder-like materials. Such clay or oxide binders have been employed normally only for the purpose of improving the crush strength of the catalyst. A particularly preferred binder for the catalyst of the present invention comprises silica.

The relative proportions of the finely divided crystalline silicate material and the inorganic oxide matrix of the binder can vary widely. Typically, the binder content of the composite catalyst ranges from 5 to 95% by weight, more typically from 20 to 50% by weight, based on the weight of the composite catalyst. Such a mixture of crystalline silicate and an inorganic oxide binder is referred to as a formulated crystalline silicate.

In mixing the catalyst with a binder, the catalyst may be formulated into pellets, extruded into other shapes, or formed into a spray-dried powder.

Typically, the binder and the crystalline silicate catalyst are mixed together by an extrusion process. In such a process, the binder, for example silica, in the form of a gel is mixed with the crystalline silicate catalyst material and the resultant mixture is extruded into the desired shape, for example pellets. Thereafter, the formulated crystalline silicate is calcined in air or an inert gas, typically at a temperature of from 200 to 900° C. for a period of from 1 to 48 hours.

The binder preferably does not contain any aluminium compounds, such as alumina. This is because as mentioned above the preferred catalyst has a selected silicon/aluminium ratio of the crystalline silicate. The presence of alumina in the binder yields other excess alumina if the binding step is performed prior to the aluminium extraction step. If the aluminium-containing binder is mixed with the crystalline silicate catalyst following aluminium extraction, this re-aluminates the catalyst. The presence of aluminium in the binder would tend to reduce the propylene selectivity of the catalyst, and to reduce the stability of the catalyst over time.

In addition, the mixing of the catalyst with the binder may be carried out either before or after any steaming step.

The various preferred catalysts have been found to exhibit high stability. This enables the catalytic conversion process to be performed continuously in two parallel "swing" reactors wherein when one reactor is operating, the other reactor is undergoing catalyst regeneration. The catalyst also can be regenerated several times. The catalyst is also flexible in that it can be employed to crack a variety of feedstocks, either pure or mixtures, coming from different sources in the oil refinery or petrochemical plant and having different compositions.

In the catalytic conversion process, the process conditions are selected in order to provide high selectivity towards propylene, a stable conversion into propylene over time, and a stable product distribution in the effluent. Such objectives are favoured by the use of a low acid density in the catalyst (i.e. a high Si/Al atomic ratio) in conjunction with a low pressure, a high inlet temperature and a short contact time, all of which process parameters are interrelated and provide an overall cumulative effect (e.g. a higher pressure may be offset or compensated by a yet higher inlet temperature). The process conditions are selected to disfavour hydrogen transfer reactions leading to the formation of paraffins, aromatics and coke precursors. The process operating conditions thus employ a high space velocity, a low pressure and a high reaction temperature.

The liquid hourly space velocity (LHSV) with respect to the composite hydrocarbon feedstock ranges from 0.5 to 30 $h^{-1}$, preferably from 1 to 20 $h^{-1}$, most preferably about 10 $h^{-1}$. The composite hydrocarbon feedstock is preferably fed at a total inlet pressure sufficient to convey the feedstock through the reactor. Preferably, the total absolute pressure in the reactor ranges from 0.5 to 50 bars, more preferably from 5 to 45 bars. The partial pressure of the aliphatic hetero compound(s) may range from 10 to 400 kPa, preferably from 20 to 380 kPa, yet more preferably from 50 to 200 kPa. A particularly preferred aliphatic hetero compound partial pressure is 100 kPa. The olefin partial pressure may range from 10 to 200 kPa. A particularly preferred olefin partial pressure is 100 kPa (approximately atmospheric pressure). The outlet pressure is typically 1.5 bara.

The weight ratio of the at least one $C_1$ to $C_6$ aliphatic hetero compound to the total hydrocarbons in the feedstock may be from 1 to 99%, more preferably from 15 to 85%, yet more preferably from 25 to 50%.

The weight ratio of the at least one $C_1$ to $C_6$ aliphatic hetero compound to the total unsaturated hydrocarbons in the feedstock may be from 0.05:1 to 20:1, more preferably from 0.25:1 to 4:1, yet more preferably from 0.5:1 to 2:1, most preferably from 0.75:1 to 1:1.

The composite hydrocarbon feedstock may be fed undiluted or diluted with steam, e.g. from 0 to 80 wt % steam, typically about 30 wt % steam, and/or in an inert gas, e.g. nitrogen or hydrogen. The use of a low aliphatic hetero compound partial pressure, for example atmospheric pressure, tends to lower the incidence of hydrogen transfer reactions in the conversion process, which in turn reduces the potential for coke formation which tends to reduce catalyst stability. Preferably, the inlet temperature of the feedstock ranges from 350 to 650° C., more preferably from 400 to 600° C., yet more preferably from 460 to 580° C., typically around 540° C. to 560° C.

The catalytic conversion process can be performed in a fixed bed reactor, a moving bed reactor or a fluidized bed reactor. A typical fluid bed reactor is one of the FCC type used for fluidized-bed catalytic cracking in the oil refinery. A typical moving bed reactor is of the continuous catalytic reforming type. As described above, the process may be performed continuously using a pair of parallel "swing" fixed bed reactors.

Since the catalyst exhibits high stability for an extended period, the frequency of regeneration of the catalyst is low. More particularly, the catalyst may accordingly have a lifetime which exceeds one year.

The light fractions of the effluent, namely the $C_2$ and $C_3$ cuts, can contain more than 90% olefins (i.e. ethylene and propylene), typically more than 90% ethylene and propylene. Such cuts are sufficiently pure to constitute chemical grade olefin feedstocks. The propylene yield in such a process can range from 35 to 45%, the propylene yield being calculated on an "olefin+$CH_2$" basis, on the assumption that each methanol molecule constitutes a "$CH_2$" source as for any olefin present in the feedstock. The propylene/ethylene weight ratio in a mixed $C_2/C_3$ fraction typically ranges from 3:1 to 9:1, more typically from 4:1 to 7:1. The propylene of the $C_3$ cut typically constitutes greater than 97 wt %, more typically greater than 98 wt % of the total $C_3$ cut (propylene and propane).

In accordance with the process of the present invention, by simultaneously converting olefinic streams and methanol into light olefins comprising ethylene and, preferentially, propylene, the heat balance of known catalytic conversion processes for converting hydrocarbon feedstocks into light olefins, in particular propylene, can be made more uniform, and in particular can be tuned to the particular reactor by selection of the composition of the total feedstock and the reactor conditions.

In the presence of the crystalline silicate catalyst of the present invention, the cracking of the one or more olefins of $C_4$ or greater into light olefins, in particular $C_2$ and $C_3$ olefins, most preferentially propylene, is an endothermic reaction. Therefore in prior olefin cracking processes, for example as disclosed in WO-A-99/29802, the heat balance needs to be carefully controlled to account for the endothermic nature of the olefin cracking process. In contrast, the catalytic conversion, using the same catalyst, of the $C_1$ to $C_6$ aliphatic hetero compounds, employed in the process of the invention, in particular methanol, which is converted into olefins and water, is an exothermic reaction. Accordingly, since the present invention comprises passing a hydrocarbon feedstock, comprising a mixture of a first portion, containing one or more olefins of $C_4$ or greater, and a second portion, containing at least one $C_1$ to $C_6$ aliphatic hetero compounds selected from alcohols, ethers, carbonyl compounds and mixtures thereof, through a reactor containing such a crystalline silicate catalyst, in order to produce an effluent containing light olefins, a thermal balance can be achieved between the simultaneously occurring exothermic and endothermic reactions. This provides operational advantages, in particular by permitting the reactor more readily to be operated under adiabatic conditions.

The present invention will now be described in greater detail with reference to the following non-limiting Examples.

EXAMPLE 1

In Example 1, a laboratory scale fixed bed reactor had provided therein a crystalline silicate catalyst of the MFI-type. The catalyst comprised silicalite which had a silicon/aluminium atomic ratio of 273 and had been produced by a de-alumination process as described hereinabove.

More specifically, the silicalite catalyst was prepared by steaming 4.2 kg of silicalite at 550° C. for a period of 48 hours with steam in a rotating laboratory furnace. Thereafter, 2 kg of the steamed silicalite was then treated with an aqueous solution of the sodium salt of ethyl diamine tetraacetic acid (EDTA-$Na_2$), there being 8.4 litres of a 0.055 molar solution thereof for the 2 kg of silicalite. The treatment was for a period of 18 hours at boiling temperature. The silicalite was then subsequently filtered and washed thoroughly with de-ionised water. This process extracted aluminium from the silicalite.

Thereafter, an extruded catalyst was prepared using a kneader, in particular a Guittard type M5 No. 2295 kneader. In particular, 1640 g of the treated silicalite, 112 g of silica powder (Degussa FK500) and 726 g of silica sol (Nyacol 2040 from EKA containing about 41% silica by weight) were mixed for a few minutes to homogonize them, and then 600 ml of distilled water was added to the mixture to obtain a paste, which was then mixed for another 30 minutes. After the 30 minute mixing time, 10 g of polyelectrolyte solution (Nalco 9779) were added to the mixture and kneaded for 1 minute. Then 30 g of methyl-hydroxy-ethyl-cellulose (Tylose from Hoechst MHB1000P2) were added. The loss on ignition (LOI) was about 33 wt %. The extruder (Alexanderwerk type AGMR No. 04231162) was equipped with a die plate aperture of 2.5 mm, which was quadralobe shaped. The paste was passed 2 to 3 times through the extruder. The resultant extrudates were air-dried over night, then dried at 110° C. for 16 hours in a drying oven with a heating rate of 60° C. per hour, and then calcined at a temperature of 600° C. for a period of 10 hours. Finally, the catalyst was subjected to ion-exchange, whereby 1740 g of the extruded catalyst was ion-exchanged using $NH_4Cl$ (0.5 molar and 7310 ml of solution) twice, the first time being for a period of 18 hours and the second time being for a period of 3 hours, both at the boiling temperature of the solution. Finally, the catalyst was filtered off, washed and calcined at a temperature of 400° C. for a period of 3 hours.

The resultant modified silicalite catalyst was in the form of particles of crushed extrudates of 35 to 45 mesh size. The surface area was 339 $m^2$/gram and pore volume was 1.1 $cm^3$/gram. The loss on ignition was 1.7 wt %. Chemical analysis of the catalyst indicate that the composition as $SiO_2$ 99.59 wt %, $Al_2O_3$ 0.31 wt %, and $Fe_2O_3$ 0.06 wt %. This provided a silicon/aluminium atomic ratio of 273. The silicalite content was 80 wt %.

The laboratory scale reactor comprised a tube which had a diameter of 11 mm and a length of 500 mm. The tube was loaded with a catalyst load of 10 ml (5.98 g). The top and bottom ends of the reactor tube were filled with ceramic inert granulates of 1.6 mm diameter. A thermocouple well was placed inside the reactor to measure the temperature profile in the catalyst bed.

The reactor was heated up at a rate of 50° C. per hour under nitrogen gas to an operating temperature of 560° C. The reactor was operated at atmospheric pressure.

The reactor was fed with feedstock as set out in Table 1 (where MW means molecular weight, O means olefins, D means dienes, P means paraffins and A means aromatics). The composite feedstock included an olefin-containing $C_4$+ fraction and a methanol fraction mixed together containing about 30 wt % methanol based on the total weight of the composite feedstock. The weight ratio of the methanol to the unsaturated hydrocarbons (olefins and dienes) in the feedstock was about 0.8:1.

The LHSV of the feedstock was 10 $h^{-1}$. The flow rate of —$CH_2$, in both the olefin-containing portion and the methanol, was 72 grams/hour. The reactor inlet temperature was adjusted to 560° C. The outlet pressure was set at 1.5 bara (150 kPa). The time or stream (TOS) was under 30 hours. The composition of the effluent was analysed on-line using an chromatograph equipment, having a microbore column of 40 m from Agilent Technologies. A second chromatographic analysis was carried out due to the correlation between isobutene and 1-butene having a Poraplot U column in a micro gas chromatograph (Micro G C) from Agilent Technologies.

After the feedstock flow was terminated following the selected time on stream, the reactor tube was purged with nitrogen and cooled down to 300° C. The catalyst was then regenerated using the sequence of steps shown in Table 2. Any reactor coke was burned of under controlled temperatures and under controlled flow rates of nitrogen and air, in particular by limiting the amount of oxygen (0.6 wt %) to control the exotherm of the carbon oxygenation reaction. Subsequently, the reactor was purged with nitrogen for a subsequent cycle. This regeneration procedure allows full recovery of the activity, selectivity and stability of the catalyst.

Figure 1:
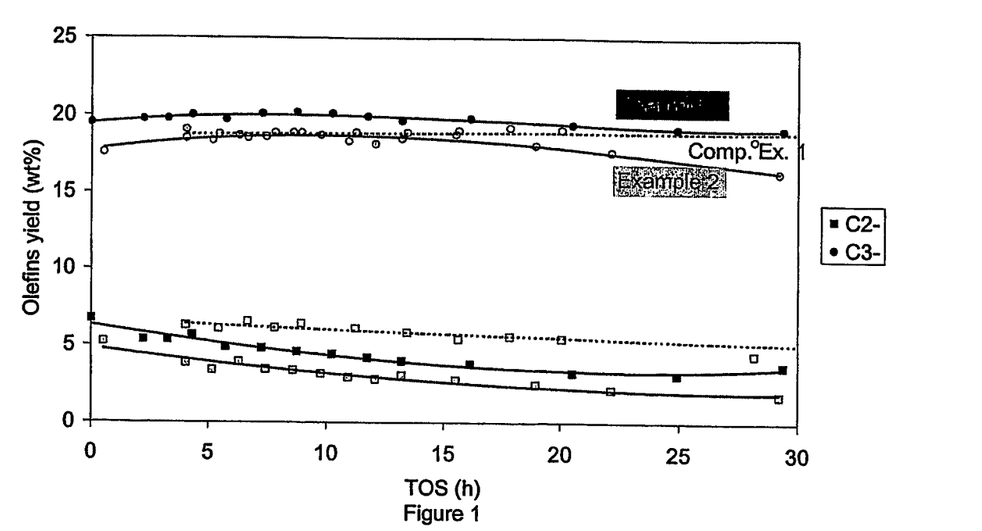
FIG. 1 shows the relationship between the yield, on an olefin basis, of ethylene and propylene in the effluent and time on stream in Examples 1 and 2 and Comparative Example 1.

FIG. 1 shows the relationship between the ethylene yield (in weight percent) and the propylene yield (in weight percent), verses time on stream (TOS) for Example 1. The olefins yield in FIG. 1 is on an olefin basis.

Figure 2:
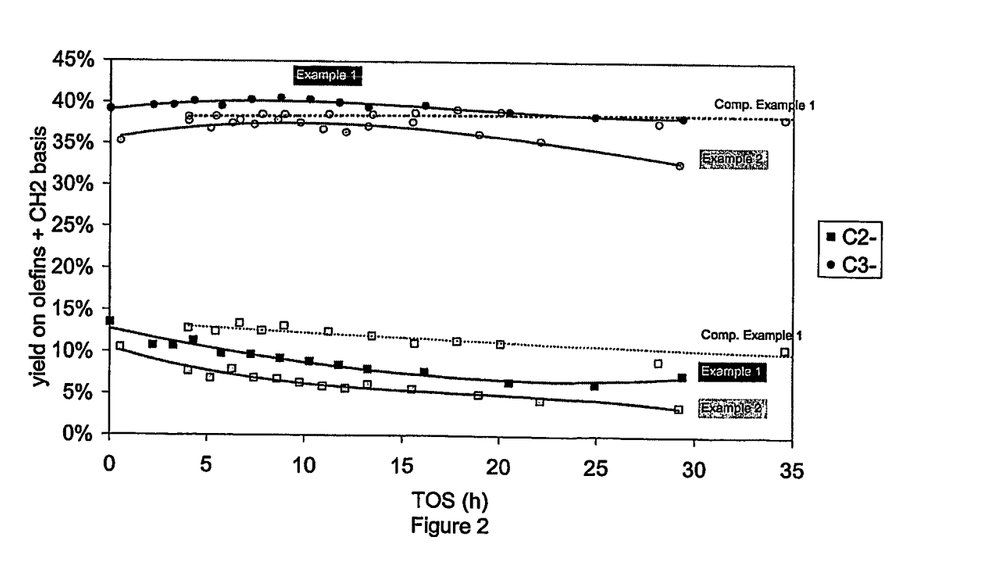
FIG. 2 shows the relationship between the yield, on an olefin+$CH_2$ basis, of ethylene and propylene in the effluent and time on stream in Examples 1 and 2 and Comparative Example 1.

In order to take into account of the contribution of methanol in Example 1 to the conversion into ethylene and propylene, the yield of both ethylene and propylene was normalised so as to be on an "olefin+$CH_2$" basis, on the assumption that each methanol molecule constitutes a "$CH_2$" source as for any olefin present in the feedstock. FIG. 2 shows the relationship between the normalised yield on an olefin+$CH_2$ basis with respect to the time on stream.

Figure 3:
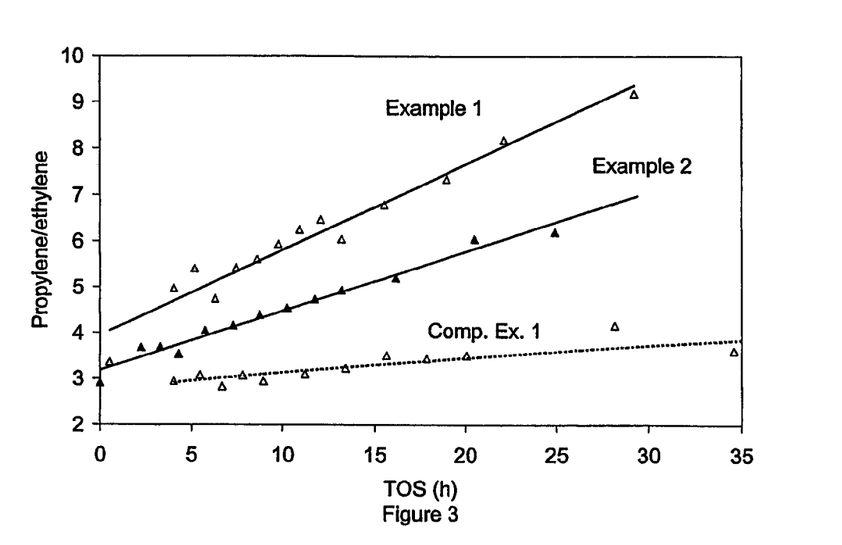
FIG. 3 shows the relationship between the propylene/ethylene ratio in the effluent and time on stream in Examples 1 and 2 and Comparative Example 1.

FIG. 3 shows the relationship between the propylene/ethylene yield ratio with respect to the time on stream.

It may be seen from FIGS. 1, 2 and 3 that the propylene/ethylene yield ratio is initially about 3 and increases to a value of greater than 5 with increasing time on stream, up to about 25 hours.

It should be noted that the methanol in the feedstock was fully converted and no methanol or dimethylether (DME) was detected in the effluent, even at the end of a cycle. The gas chromatography results employed to derive the data for FIGS. 1 to 3 were converted to obtain the olefin yield taking into account that water was not detected in the effluent, using a flame ionization detector.

Figure 4:
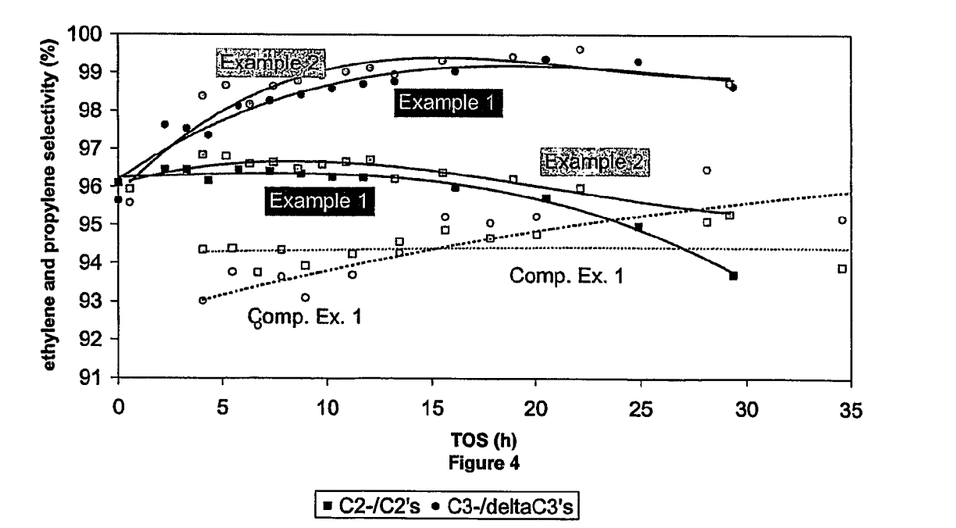
FIG. 4 shows the relationship between the olefin purity, for both propylene and ethylene, in the effluent and time on stream in Examples 1 and 2 and Comparative Example 1.

FIG. 4 shows the relationship between the composition of the $C_2$ and $C_3$ fractions in the effluent versus time on stream. The $C_2$ fraction shows the proportion, by weight, of ethylene to total $C_2$'s and the proportion, by weight, of propylene to total $C_3$'s for the $C_2$ and $C_3$ fractions respectively.

EXAMPLE 2

In Example 2 the process of Example 1 was repeated with the same feedstock, catalyst flow rate and LHSV but at a lower reactor inlet temperature of 540° C. The corresponding results are also shown in FIGS. 1 to 4.

COMPARATIVE EXAMPLE 1

In this Comparative Example, Example 1 was repeated using the same catalyst but a different feedstock that did not contain methanol, and had the hydrocarbon composition shown in Table 3. This feedstock was the same as that of the olefin-containing fraction employed to produce the composite feedstock of Examples 1 and 2, but did not include the 30 wt % addition methanol. The olefin content of the feedstock was correspondingly higher than that of the olefin-containing portion of the composite feedstock additionally including a methanol portion, used in Examples 1 and 2. The $CH_2$ flow rate was 60 g/h, and the LHSV was as in Example 1. The reactor temperature was 560° C. The corresponding results are also shown in FIGS. 1 to 4.

A comparison of the results, illustrated in FIGS. 1 to 4 for Examples 1 and 2 and Comparative Example 1, shows that by replacing a proportion, in the Examples 30 wt %, of an olefin-containing hydrocarbon feed, containing about 50 wt % olefins, with methanol can give rise to a slight increase in propylene yield at the same inlet temperature. However, as also shown in FIGS. 1 and 2, the additional of methanol to the olefin-containing feedstock reduces the ethylene yield quite significantly, particularly after about 10 hours on stream. Also, if the inlet temperature is decreased, in the Examples from 560° C. to 540° C., when methanol is added to the olefin-containing portion, the ethylene and propylene yields are correspondingly decreased, but the propylene yield at 540° C. remains at substantially the same level as the propylene yield for the olefin-containing hydrocarbon feedstock without methanol at a higher inlet temperature of 560° C.

From FIG. 2 it may be seen that for the normalised yield on an "olefin+$CH_2$" basis, the relationship between ethylene and propylene yield are substantially the same as shown in FIG. 1. Comparing Example 1 with Comparative Example 1, which were conducted at the same reactor inlet temperature, the presence of methanol has a slight positive impact on the propylene yield, and lowers the ethylene yield.

FIG. 3 shows that whether the reactor inlet temperature is the same (example 1), or lower (Example 2), the propylene/ethylene yield ratio is increased by adding methanol to an olefin-containing hydrocarbon feedstock. This is because of reduced ethylene production as a result of the addition of methanol. Furthermore, the propylene/ethylene ratio tends progressively to increase with time on stream, due to progressive reduction in the ethylene production with increasing time on stream when methanol has been added to the olefin-containing hydrocarbon feedstock. Furthermore, if the reactor inlet temperature is decreased together with addition of methanol to the olefin-containing hydrocarbon feedstock, the propylene/ethylene yield ratio tends to be increased.

In FIG. 4, it may be seen that the presence of methanol in the hydrocarbon feedstock tends to enhance the selectivity towards olefins for both the $C_2$ and $C_3$ fractions. This means that for the $C_3$ cut, the propylene purity is improved, and for the $C_2$ cut the ethylene purity is improved.

In summary therefore, the Examples and Comparative Examples demonstrate that olefinic streams and methanol can be simultaneously converted into light olefins. The use of methanol co-injection gives rise to slightly higher propylene yields, at the same reactor inlet temperature. More importantly, a higher propylene/ethylene yield ratio can be achieved by methanol co-injection and furthermore, the olefin contents in the light $C_2$ and $C_3$ cuts can be significantly improved.

Figure 5:
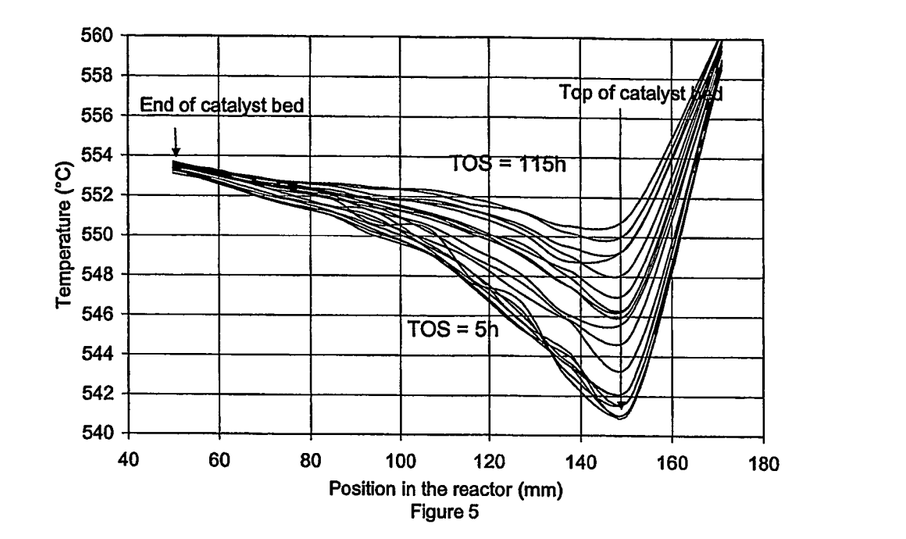
FIG. 5 shows the relationship between temperature and position in the reactor in Comparative Example 1.

FIG. 5 shows the relationship between temperature and position in the reactor in Comparative Example 1, with there being a plurality of plots, each taken at a specific time on stream, from the beginning to the end of the conversion process (the final time on stream being about 115 hours). The curves progressively move as shown in FIG. 5 between the beginning of the time on stream to the end of the time on stream. Even though in Comparative Example 1 the reactor was not operated in adiabatic mode, it may clearly be seen that the hydrocarbon feedstock, which was introduced at 560° C., entered the top of the catalyst bed, but the temperature at the top of the catalyst bed decreased abruptly as soon as the olefin cracking reaction occurred at the top of the catalyst bed. The amplitude of the "negative" temperature peak was deepest at the beginning of the time on stream, and decreased progressively at the catalyst tended progressively to deactivate. However, the minimum temperature value for each plot remained substantially at the same position with increasing time on stream. This clearly shows that the olefinic catalytic conversion is endothermic, and leads to a thermal imbalance in the reactor.

Figure 6:
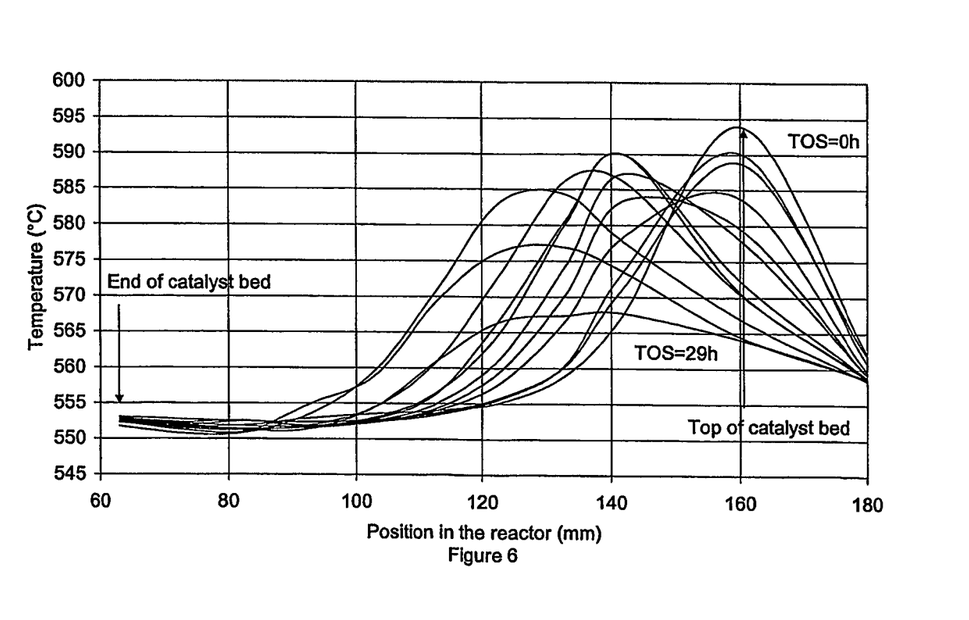
FIG. 6 shows the relationship between temperature and position in the reactor in Example 1.

In contrast, FIG. 6 shows a similar relationship between temperature and position in the reactor, but for Example 1, where the reactor inlet temperature was the same at 560° C. as for Comparative Example 1, but the hydrocarbon feedstock included methanol as well as the one or more olefins of $C_4$ or greater. Again, a plurality of plots are shown varying with time on stream, and ranging from the beginning of the time on stream to the end of the time on stream, at about 29 hours. It may be seen from FIG. 6 that the temperature increased sharply at the top of the catalytic bed, which indicates that the methanol reacted first as the composite hydrocarbon feedstock entered the reactor. The methanol conversion reaction is exothermic, which caused the increase in temperature. With increasing time on stream leading to progressive deactivation of the catalyst, the temperature peak decreased and was displaced from the top of the catalyst bed at least partially towards the end of the catalyst bed.

Comparing FIGS. 5 and 6, it will be seen that for typical operational times on stream of more than 10 hours, the temperature profile in the catalyst bed is more uniform, indicating a greater degree of heat balance between the competing exothermic and endothermic reactions, for the process of the invention, as compared to the Comparative Example where only an endothermic reaction of olefin catalytic conversion occurs.

TABLE 1

| | |
|---|---|
| Methanol (wt %) | 30.03 |
| Paraffins (wt %) | 31.22 |
| Olefins (wt %) | 36.54 |
| Dienes (wt %) | 0.69 |
| Aromatics (wt %) | 1.53 |
| Average MW | 50.4 |
| Olefinicity (wt %) | |
| O2 + D2/(O2 + D2 + P2) | — |
| O3 + D3/(O3 + D3 + P3) | — |
| O4 + D4/(O4 + D4 + P4) | 55.6 |
| O5 + D5/(O5 + D5 + P5) | 60.0 |
| O6 + D6/(O6 + D6 + P6 + A6) | 48.4 |
| O7 + D7/(O7 + D7 + P7 + A7) | 39.7 |
| O8 + D8/(O8 + D8 + P8 + A8) | 43.5 |

TABLE 2

| Temperature | Nitrogen (NL/h) | Air (NL/h) |
|---|---|---|
| 310° C. | 30 | — |
| Ramp 50° C./h | 31.5 | 0.9 |
| 500° C., 6 h | 31.5 | 0.9 |
| 560° C. | 31.5 | 0.9 |
| 560° C. 10 h | 31.5 | 0.9 |
| 560° C. | 30 | — |

TABLE 3

| | |
|---|---|
| Paraffins (wt % | 45.28 |
| Olefins (wt %) | 48.95 |
| Dienes (wt %) | 0.89 |
| Aromatics (wt %) | 4.89 |
| Average MW | 66.8 |

TABLE 3-continued

| | |
|---|---|
| Olefinicity (wt %) | |
| O2 + D2/(O2 + D2 + P2) | — |
| O3 + D3/(O3 + D3 + P3) | — |
| O4 + D4/(O4 + D4 + P4) | 55.6 |
| O5 + D5/(O5 + D5 + P5) | 60.0 |
| O6 + D6/(O6 + D6 + P6 + A6) | 48.4 |
| O7 + D7/(O7 + D7 + P7 + A7) | 39.7 |
| O8 + D8/(O8 + D8 + P8 + A8) | 43.5 |

The invention claimed is:

1. A process for converting a hydrocarbon feedstock to provide an effluent containing light olefins, the process comprising passing a multicomponent feedstock comprising a mixture of a first portion, containing at least one olefin of $C_4$ or greater, and a second portion containing at least one $C_1$ to $C_6$ aliphatic hetero compound selected from the group consisting of an alcohol, an ether and a carbonyl compound and mixtures thereof, through a reactor containing a crystalline silicate catalyst selected from the group consisting of an MFI crystalline silicate having a silicon/aluminium atomic ratio of at least 180 and an MEL crystalline silicate having a silicon/aluminium atomic ratio of from 150 to 800 which has been subjected to a steaming step, to produce an effluent comprising a molar excess of propylene,
wherein the reactor is operated adiabatically, wherein at least a portion of the olefin of $C_4$ or greater undergoes an endothermic cracking reaction, at least a portion of the $C_1$ to $C_6$ aliphatic hetero compound undergoes an exothermic reaction to form light olefins, and a thermal balance is exhibited between the simultaneous exothermic reaction and endothermic reaction, and wherein the propylene/ethylene molar ratio in the effluent is greater than the propylene/ethylene molar ratio of the process without the addition of the $C_1$ to $C_6$ aliphatic hetero compound and the propylene/ethylene molar ratio is at least 3.

2. The process of claim 1 wherein the weight ratio of the at least one $C_1$ to $C_6$ aliphatic hetero compound in the second portion to the total hydrocarbons in the first and second portions of the feedstock is within the range 15 to 85 percent.

3. The process of claim 2 wherein the weight ratio of the at least one $C_1$ to $C_6$ aliphatic hetero compound in the second portion to the total hydrocarbons in the first and second portions of the feedstock is within 25 to 50 percent.

4. The process of claim 1 wherein the weight ratio of the at least one $C_1$ to $C_6$ aliphatic hetero compound in the second portion to the total unsaturated hydrocarbons in the first portion of the feedstock is within the range of 0.5:1 to 2:1.

5. The process of claim 4 wherein the weight ratio of the at least one $C_1$ to $C_6$ aliphatic hetero compound in the second portion to the total unsaturated hydrocarbons in the first portion of the feedstock is within the range of 0.75:1 to 1:1.

6. The process of claim 1 wherein the second portion of the hydrocarbon feedstock contains at least one hetero compound selected from the group consisting of methanol, ethanol, dimethyl ether, diethyl ether and mixtures thereof.

7. The process of claim 6 wherein the second portion of the multicomponent feedstock comprises methanol.

8. The process of claim 6 wherein steam is supplied to the reactor.

9. The process of claim 8 wherein said feedstock contains steam in an amount up to 80 weight percent of said feedstock.

10. The process of claim 1 wherein the multicomponent feedstock is passed over said crystalline silicate catalyst at a reactor inlet temperature within the range 460° to 580° C.

11. The process of claim 10 wherein the multicomponent feedstock is passed over the crystalline silicate catalyst at a reactor inlet temperature within the range 540° to 560° C.

12. The process of claim 10 wherein the feedstock is passed over the crystalline silicate catalyst at a LHSV within the range of 1 to 20 h$^{-1}$.

13. The process of claim 10 wherein the partial pressure of the at least one or more olefins in the feedstock when passed over the crystalline silicate catalyst is within the range of 10 to 200 kPa.

14. The process of claim 13 wherein the partial pressure of the at least one $C_1$ to $C_6$ aliphatic hetero compound in the feedstock when passed over the crystalline silicate catalyst is within the range of 10 to 400 kPa.

15. The process of claim 1 wherein the crystalline silicate catalyst comprises silicalite having a silicon/aluminum atomic ratio of from 250 to 500.

16. The process of claim 15 wherein the first portion of said feedstock includes at least one of a hydrotreated raw $C_4$ feedstock, LCCS, a raffinate 2 feedstock, a raffinate 1 feedstock, a raffinate 2 feedstock from a methyl tert-butyl ether (MTBE) or an ethyl tert-butyl ether (ETBE) unit, a raffinate from an olefins metathesis unit, or a hydrotreated olefin-containing stream from an FCC unit, a visbreaker or a delayed coker.

17. The process of claim 15 wherein the first portion of said feedstock includes a product, which contains $C_{4+}$ olefins, of a methanol-to-olefins (MTO) process.

18. The process of claim 1 wherein a fraction of the effluent which contains $C_{4+}$ olefins is recycled back through the reactor to provide at least a part of the first portion of the multicomponent feedstock.

19. The process of claim 1 wherein said second portion of said feedstock includes methanol and the weight ratio of the methanol in the second portion to the total unsaturated hydrocarbons in the first portion of said feedstock is from 0.5:1 to 2:1, and the reactor inlet temperature is from 540° to 560° C.

20. The process of claim 19 wherein said crystalline silicate catalyst comprises silicalite having a silicon/aluminium atomic ratio at from 250 to 500.

* * * * *